United States Patent
Badri et al.

(10) Patent No.: US 9,593,983 B2
(45) Date of Patent: Mar. 14, 2017

(54) MEASURING HYDROCARBON CONTENT OF A ROCK FORMATION DOWNHOLE USING LASER-INDUCED VAPORIZATION AND PYROLYSIS

(71) Applicant: SCHLUMBERGER TECHNOLOGY CORPORATION, Sugar Land, TX (US)

(72) Inventors: Mohammed Badri, Al-Khobar (SA); Reza Taherian, Al-Khobar (SA)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 151 days.

(21) Appl. No.: 14/477,740

(22) Filed: Sep. 4, 2014

(65) Prior Publication Data

US 2016/0069177 A1    Mar. 10, 2016

(51) Int. Cl.
 *E21B 47/10*   (2012.01)
 *G01J 5/00*    (2006.01)
 *E21B 49/00*   (2006.01)

(52) U.S. Cl.
 CPC .......... *G01J 5/00* (2013.01); *E21B 49/00* (2013.01)

(58) Field of Classification Search
 CPC ............................... E21B 47/102; G01J 5/00
 USPC ......................................... 324/338, 344, 345
 See application file for complete search history.

(56) References Cited

U.S. PATENT DOCUMENTS

| | | | |
|---|---|---|---|
| 5,416,024 A | 5/1995 | Smith | |
| 5,912,459 A | 6/1999 | Mullins et al. | |
| 7,458,257 B2 | 12/2008 | Pop et al. | |
| 2008/0198375 A1 | 8/2008 | DiFoggio | |
| 2010/0181471 A1* | 7/2010 | Pop | G01V 9/00 250/254 |
| 2012/0000279 A1* | 1/2012 | Daniel | E21B 49/10 73/152.28 |

(Continued)

OTHER PUBLICATIONS

Dessort et al., "SPE 161626: Enhanced Assessment of the Distribution of Organic Matter in Unconventional Plays and Tarmat in Reservoirs Using a New Laser Pyrolysis Method on Core," SPE International, 2012: pp. 1-5.

(Continued)

*Primary Examiner* — Jay Patidar
(74) *Attorney, Agent, or Firm* — Bridget M. Laffey; Jakub Michna

(57) ABSTRACT

A downhole tool to make one or more downhole measurements of laser-induced vaporization and/or pyrolysis of hydrocarbons is provided and disposed at a desired location within a wellbore. A tool head of the downhole tool is brought into sealing engagement with the wellbore wall. The fluid within an interior region enclosed by the tool head and the wellbore wall is evacuated and a measurement spot is irradiated with a laser to generate volatile hydrocarbons and/or pyrolytic hydrocarbons. Measurements are made on the volatile hydrocarbons and/or pyrolytic hydrocarbons and one or more formation properties are inferred based on the measurements. A low level of laser radiation intensity, irradiating some or all of the wellbore wall enclosing the interior region, may be used to prevent measurement contamination, and both medium power and high power levels of laser radiation may be used to first vaporize and then pyrolyze the hydrocarbons.

14 Claims, 4 Drawing Sheets

(56) References Cited

U.S. PATENT DOCUMENTS

2012/0312530 A1 12/2012 Pope et al.
2013/0014943 A1 1/2013 Harrison et al.

OTHER PUBLICATIONS

Patterson et al., "SPE-169784-MS: Pre-Production Deployed Scale Inhibition Treatments in Deep-Water, West Africa," SPE International, 2014: pp. 1-45.
International Search Report and Written Opinion for corresponding PCT Application Serial No. PCT/US2015/047874, dated Nov. 25, 2015, 20 pages.

* cited by examiner

MEASURING HYDROCARBON CONTENT OF A ROCK FORMATION DOWNHOLE USING LASER-INDUCED VAPORIZATION AND PYROLYSIS

BACKGROUND

Total organic carbon (TOC) is a commonly sought property of a hydrocarbon-bearing subsurface formation. In recent years the level of interest in the measurement of this property has increased even further with the emergence of shale oil and shale gas exploration and production. The shale formations being explored are typically more complex than conventional reservoir formations and they pose many more challenges in their petrophysical studies and interpretations. Many of the standard measurement techniques commonly used in conventional formations, such as measuring the TOC, do not work in shale.

Shale formations are highly laminated and their depositional histories and transformation processes generally vary. The lamination thickness is not constant, but rather may vary anywhere in the range of millimetres to meters. As a result, higher resolution measurements with short spacings between the sampling points is important for evaluating the shales and to ensure any decision on the quality and economic potential of the formation reflects the real system.

Laser induced pyrolysis (LIP) has been used to make certain formation evaluation measurements uphole, at the surface. For example, LIP has been applied to core samples. However, that method may only be used if a well is cored, which is not particularly common. LIP may also be used on rock cuttings flushed to the surface while drilling. However, one generally has no idea of the depth within the well from which the cutting came. That is, during drilling operations pieces of rock are cut and brought to the surface by the circulating drilling fluid (mud). While the mud travels to the surface, it experiences turbulent flow, causing the cuttings to mix and their relative depth information to be lost. In relatively homogeneous formations, measurements at the surface may succeed. However, shale cuttings, with their associated variable laminations, should not be considered to be from a homogeneous formation. A LIP measurement on a cutting may provide a high resolution map of the lamination of that cutting, albeit with uncertain depth information, but the obtained lamination map is generally not representative of the lamination of the shale reservoir.

SUMMARY

A downhole tool to make one or more downhole measurements of laser-induced vaporization and/or pyrolysis of hydrocarbons is provided and disposed at a desired location within a wellbore. A tool head of the downhole tool is brought into sealing engagement with the wellbore wall. The fluid within an interior region enclosed by the tool head and the wellbore wall is evacuated and a measurement spot is irradiated with a laser to generate volatile hydrocarbons and/or pyrolytic hydrocarbons. Measurements are made on the volatile hydrocarbons and/or pyrolytic hydrocarbons and one or more formation properties are inferred based on the measurements. A low level of laser radiation intensity, irradiating some or all of the wellbore wall enclosing the interior region, may be used to prevent measurement contamination, and both medium power and high power levels of laser radiation may be used to first vaporize and then pyrolyze the hydrocarbons.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. Embodiments are described with reference to the following figures. The same numbers are generally used throughout the figures to reference like features and components.

DETAILED DESCRIPTION

Figure 1:
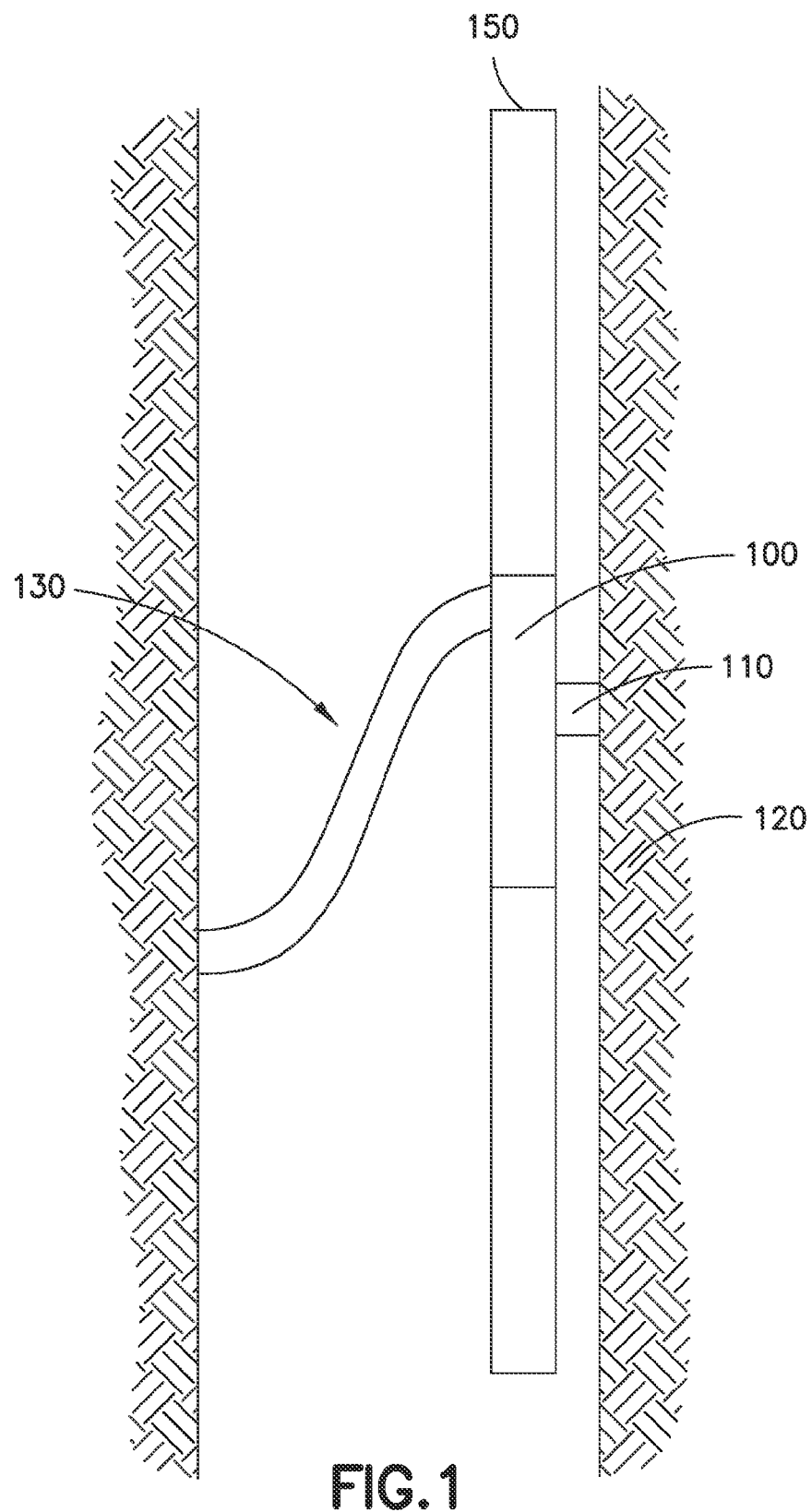
FIG. 1 is a schematic drawing of one embodiment of a laser-induced vaporization and pyrolysis measurement apparatus deployed in a wellbore, in accordance with the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Some embodiments will now be described with reference to the figures. Like elements in the various figures may be referenced with like numbers for consistency. In the following description, numerous details are set forth to provide an understanding of various embodiments and/or features. However, it will be understood by those skilled in the art that some embodiments may be practiced without many of these details and that numerous variations or modifications from the described embodiments are possible. As used herein, the terms "above" and "below," "up" and "down," "upper" and "lower," "upwardly" and "downwardly," and other like terms indicating relative positions above or below a given point or element are used in this description to more clearly describe certain embodiments. However, when applied to equipment and methods for use in wells that are deviated or horizontal, such terms may refer to a left to right, right to left, or diagonal relationship, as appropriate. It will also be understood that, although the terms first, second, etc., may be used herein to describe various elements, these elements should not be limited by these terms. These terms are only used to distinguish one element from another.

The terminology used in the description herein is for the purpose of describing particular embodiments only and is not intended to be limiting. As used in the description and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

A system and method to measure the hydrocarbon content of a rock formation at a downhole location is disclosed. A specially designed apparatus capable of performing the operation downhole is used. Performing the measurements downhole avoids complications such as unwanted evaporation or drying of the core or other "live" sample versus "dead" sample issues that may arise when a core or cutting is brought to the surface. A (medium power) laser beam may be used to cause the more volatile hydrocarbons in a formation to vaporize (i.e., evaporate or boil). The vaporized hydrocarbons are pumped into a measurement chamber in the tool and measured using a plurality of techniques. The laser power may then be increased, causing a higher local temperature that in turn causes the heavier, less volatile hydrocarbons to undergo pyrolysis, thereby producing smaller, more volatile compounds (pyrolytic hydrocarbons) that can be pumped into the tool and quantified. Performing the vaporization and pyrolysis and making the measurements downhole avoids the problem of relating the sample to the depth from which it was generated. Because the LIP measurement is made downhole, the sequence of measurements is known and the distances between adjacent measurement points are well characterized. Also, because the LIP measurement is made downhole, a processor carried on the tool may be used to control operation of the tool and to store information in memory.

Pyrolysis uses thermal energy to raise the temperature of a sample. At relatively lower temperatures (up to about 300° C.), medium size molecules vaporize and can be detected. At higher temperatures, the heat causes the larger molecules, which are not volatile at any (reasonably achievable) temperature (given the typical ambient pressures), to undergo cracking by breaking some of their bonds. This causes the larger molecule to break into a few smaller, more volatile, molecules that can be vaporized and be detected.

If the source of thermal energy is a laser, then the process is called LIP. The laser is usually chosen to be in the infrared wavelength range because in this wavelength range the optical energy converts more easily to heat than at other wavelengths. Lasers in the power range of tens of watts are readily available from many vendors and may be appropriate for this application. These units are small to be readily incorporated into a downhole tool without any need to modify the laser itself Lasers with more power are also commercially available and can be used for this application if they are engineered to fit within the space requirements of a downhole tool. Infrared lasers are commonly used for metal welding, which requires much more power than is generally needed to crack a large hydrocarbon molecule. A 50-watt laser, for example, may focus the light energy in a spot size of about 1 mm by 1 mm. The power density in the spot is equivalent to 5000 watts/cm$^2$ or 50 megawatts/m$^2$, which is more power than the 20 megawatts/m$^2$ that has been used successfully to perform uphole LIP.

The laser beam can be brought close to the target point using optical fiber as is common in the art. If desired, using a lens with appropriate focal length, the beam can also be focused to smaller cross sections, thereby increasing the power density. The focusing increases the power density at the expense of a smaller spot size.

A downhole LIP tool 100 is shown in FIG. 1. Tool 100 may be part of a larger string of tools 150 depending on the application, and is equipped with a head 110 that contacts and hydraulically seals against the formation or borehole wall 120. Since the borehole is usually filled with drilling fluid that can interfere with LIP operations, a small spot on the wall is isolated from the borehole environment by pressing the head 110 against the borehole wall. Hydraulically isolating a small section of the borehole wall is routinely done by the sampling tools that seal against the wall and pump a fluid sample out of the formation. In some applications, such as a wireline tool, a bow spring 130 may be used to press the head 110 (which may be equipped, for example, with an elastic (rubber) sealing material on its edge) firmly against the borehole wall 120. Alternatively, tool head 110 may be pressed against the borehole wall 120 using hydraulically energized members on the opposite side (i.e., opposite to head 110) of tool 100, as is common in sampling tools. In LWD applications, tool 100 is part of a drill string, and a pressing mechanism similar to bow spring 130 may be used, but generally with a larger spring force so that the drill string (or at least a portion of it) can be decentered in the wellbore and head 110 pressed against borehole wall 120. In another embodiment, head 110 may be telescopic and can be pressed against the borehole wall 120 without the need to decenter tool 100. In yet another embodiment, the head 110 may be part of a spring loaded pad (as is common in wireline tools) that is normally closed but can be released to extend radially and press against the borehole wall. In yet another embodiment, the head 110 may be located in a space between two packers that are used to isolate a section of the borehole.

Figure 2:
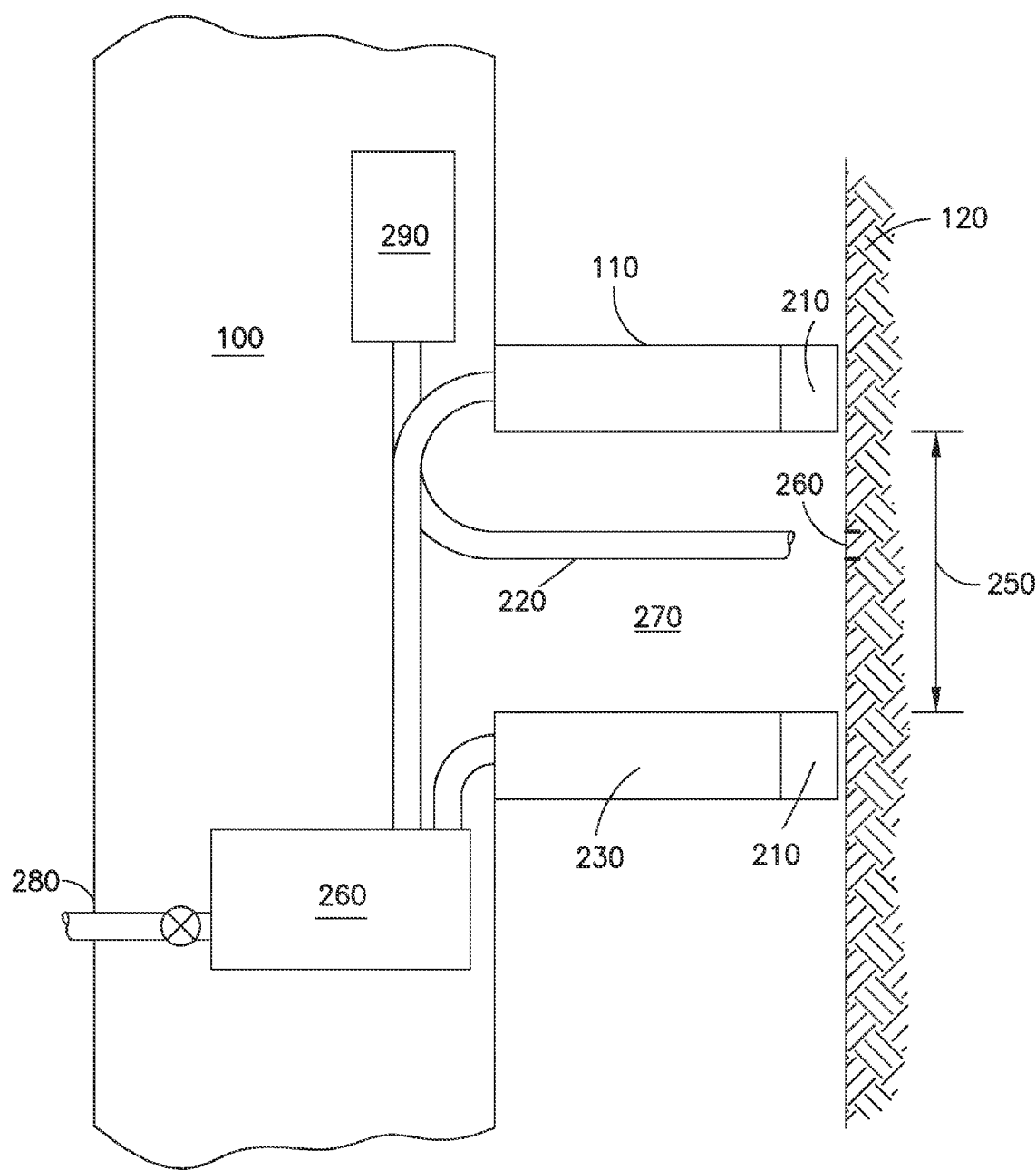
FIG. 2 is a schematic drawing of one embodiment of the measurement head of the laser-induced vaporization and pyrolysis measurement apparatus of FIG. 1, in accordance with the present disclosure.

Head 110 is shown in further detail in FIG. 2. An elastic ring 210 is attached to the outer face of head 110 that, when pressed against the borehole wall 120, helps to form a hydraulic seal. The body 230 of head 110 can be designed to be telescopic for particular implementations in which the tool 100 does not decenter in the borehole. Note the isolated area 250 is usually larger than the size of the measurement spot 260. A laser 290 is provided in the body of tool 100 and is capable of delivering the required optical power. An optical fiber 220 delivers the laser light to the measurement spot 260. The area of the measurement spot 260 is used to define the resolution of the LIP measurement.

Figure 3:
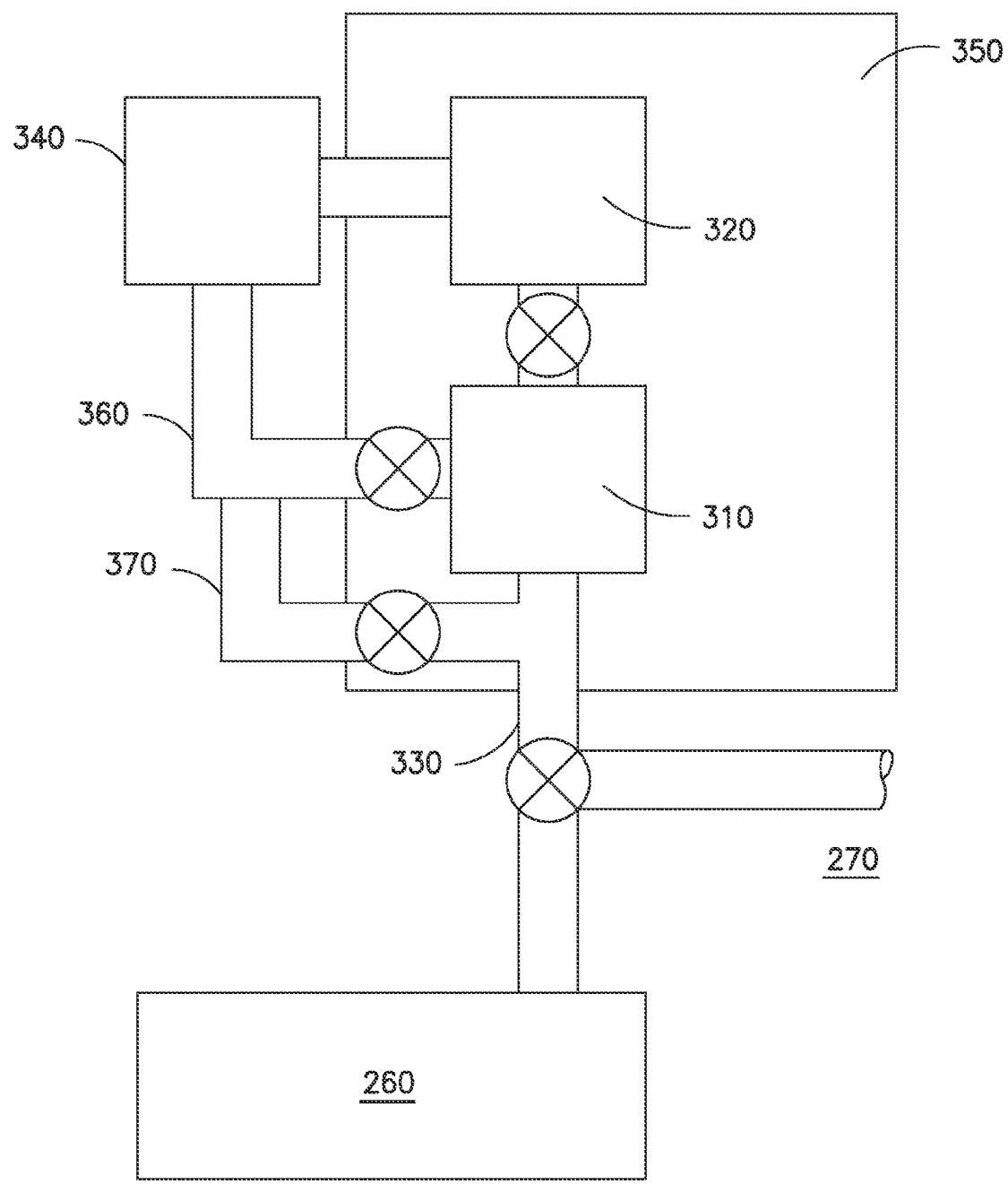
FIG. 3 s a schematic drawing of one embodiment of the measurement device of the laser-induced vaporization and pyrolysis measurement apparatus of FIG. 1, in accordance with the present disclosure.

Once head 110 is in contact with the borehole wall and hydraulic isolation is established, a pump 260, residing in tool 100, is used to remove any borehole fluid and possibly solid particles from the volume 270 between the borehole wall 120 and the tool 100 within the region isolated by head 110. While the volume 270 contains borehole fluid, the valve 330 (shown in FIG. 3) is actuated to direct the fluid into pump 260. Pump 260 removes the undesired fluid and discharges it back to the borehole using an exhaust pipe (port) and valve 280. Once the volume 270 is empty, LIP operations can commence.

Applying thermal power (via the laser) to the formation generates volatile hydrocarbons that may be pumped away from spot 260 and into tool 100 for measurement. Once the borehole fluid is removed and laser 290 is activated, valve 330 is actuated to redirect the volatile hydrocarbons to measurement system 350. A second pump 340 is activated to facilitate the flow into measurement system 350. In other embodiments pump 260 can be used for both stages, eliminating the need for second pump 340. Measurement system 350 comprises a solid separator 310, such as an electrostatic solid separator, and a measurement module 320. The electrostatic solid separator 310 uses electrostatic energy to charge the solid particles, if any, and absorb them in a capacitor, thereby removing them from the gas stream. Alternatively, a physical filtration system such as a screen (i.e., tight mesh or tightly packed particles) could be used. It is a good practice to remove those solids since the high power laser may cause some of the still solid hydrocarbons and rock solids to vaporize and interfere with the measurements.

The measurement module 320 in measurement system 350 is used to measure the volatile hydrocarbons. Different techniques may be used to measure the volatile hydrocarbons. For example, one may use the techniques traditionally used in mass spectrometry. In an embodiment in which a mass spectrometer is used, a small fraction of the gas is delivered to the mass spectrometer, which ionizes the delivered gas and then sends the ionized gas through a mass filter. The mass filter blocks all ions except the specific component(s) of the mixture having a selected mass (i.e., m/z where z is the charge). The ions that pass through the mass filter impinge on a detector that provides the intensity or a number proportional to the number of ions. The mass selection is varied and at each selection the mass intensity is recorded, leading to a spectrum that can be analyzed to identify and determine the concentration of individual hydrocarbons in the mixture. Use of a mass spectrometer for downhole applications has been suggested previously in U.S. Pat. No. 7,458,257.

In some applications, the detailed information about the components of the gas may not be needed. For example, only the total organic (i.e., hydrocarbon) content (TOC) may be of interest. In these cases there is no need to identify the individual components—only the total carbon content is determined. For such applications a further embodiment provides a photoionization detector (PID) as part of the measurement module 320. The PID uses high energy photons such as ultraviolet radiation to ionize the sample, but instead of measuring the ions based on their mass (as was done by the mass spectrometer), the total conductivity of the ionized sample is measured and used as an indication of the number of ions. Thus, a current is injected into the chamber where the ions are present and an ampere meter is used to measure how much current passes through the chamber. The higher the number of ions, the more current can pass through and this proportionality is used to infer the concentration of ions.

In another embodiment, a thermal conductivity detector (TCD) is used to measure the hydrocarbon gas. This is another detector traditionally used in mass spectroscopy, but it can also be used as an independent device. The device is equipped with a heating solenoid and a thermal detector. In the absence of any gas in the detector, there is a background detector signal. Once gas is introduced into the detector, the thermal conductivity of the space between the heater and the detector changes, which causes a different detector signal level that can be calibrated and used to measure the relative concentrations of hydrocarbons in the gas.

The amount of laser power applied can be programmed as needed. In up-hole applications, it is common to first use a low power level illumination to remove any hydrocarbons that may be on the sample surface. That is followed by a high power level illumination that is used to vaporize the volatile hydrocarbons and pyrolyze the heavier hydrocarbons up to some depth of penetration into the sample. For downhole applications, it may be desirable to apply the laser power in three processes. In a first process, a low power laser pulse is used to clean the formation surface, as above. This may be needed since the borehole environment may contain hydrocarbons from other sources not related to the formation (such as oil base drilling fluid). In a second process, a medium power level illumination is used that penetrates into the formation and heats the volatile hydrocarbons (as used herein, "volatile hydrocarbons" means hydrocarbons that can be evaporated or boiled without being pyrolyzed). In a third process, the laser is used at high power levels that penetrate the formation and crack (pyrolyze) the larger hydrocarbons.

Figure 4:
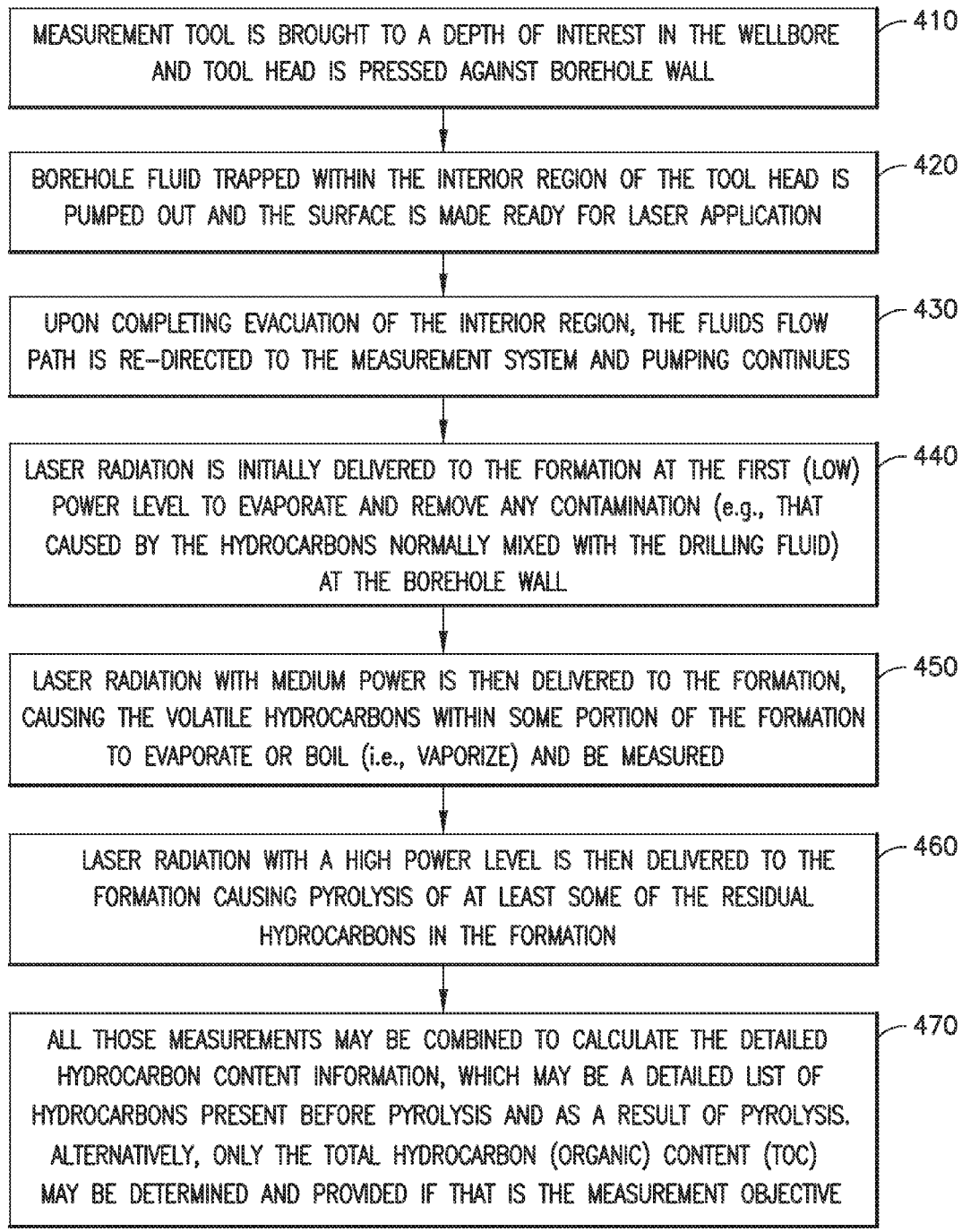
FIG. 4 is a workflow showing an embodiment of making measurements using the laser-induced vaporization and pyrolysis measurement apparatus of FIG. 1, in accordance with the present disclosure.

FIG. 4 shows a workflow of an embodiment to make a downhole measurement of laser-induced vaporization and pyrolysis, in accordance with this disclosure. Tool 100 is brought to a depth of interest in the wellbore and tool head 110 is pressed (i.e., sealingly engaged) against borehole wall 120 (410). The wellbore depth may be determined, for example, using an accompanying gamma ray tool (not shown). Next, the borehole fluid trapped within the interior region of tool head 110 is pumped out (using pump 340) and the surface is made ready for laser application (420). Upon completing evacuation of the interior region, the fluid flow path is re-directed to measurement system 350 and pumping continues (430). If desired, by-pass tube 360 and/or by-pass tube 370 may be used to divert the gas and solid from entering measurement module 320. The laser radiation is initially delivered to the formation at the first (low) power level to evaporate and remove any contamination (e.g., that caused by the hydrocarbons normally mixed with the drilling fluid) at the borehole wall 120 (440). The laser radiation with medium power is then delivered to the formation, causing the volatile hydrocarbons within some portion of the formation to evaporate or boil (i.e., vaporize) and be measured (450). The laser radiation with high power is then delivered to the formation, causing pyrolysis of at least some of the residual hydrocarbons in the formation (460). All those measurements may be combined to calculate the detailed hydrocarbon content information, which may be a detailed list of hydrocarbons present before pyrolysis and as a result of pyrolysis (470). Alternatively, only the total hydrocarbon (organic) content (TOC) may be calculated and provided if that is the measurement objective.

Some of the methods and processes described above, including processes, as listed above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions, and alterations herein without departing from the scope of the present disclosure.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

While only certain embodiments have been set forth, alternatives and modifications will be apparent from the above description to those skilled in the art. These and other alternatives are considered equivalents and within the scope of this disclosure and the appended claims. Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method, comprising:
providing a downhole tool to make one or more downhole measurements of laser-induced vaporization and/or pyrolysis of hydrocarbons, and disposing the downhole tool at a desired location within a wellbore;
bringing a tool head of the downhole tool into sealing engagement with a wall of the wellbore;
evacuating fluid within an interior region enclosed by the tool head and the wellbore wall;
irradiating a measurement spot with a laser to generate volatile hydrocarbons and/or pyrolytic hydrocarbons;
making measurements on the volatile hydrocarbons and/or pyrolytic hydrocarbons; and
inferring one or more formation properties based on the measurements.

2. The method of claim 1, further comprising irradiating with a low level of laser radiation some or all of the wellbore wall enclosing the interior region.

3. The method of claim 2, wherein irradiating a measurement spot with a laser comprises irradiating with a medium power level of laser radiation some depth into a formation.

4. The method of claim 3, wherein irradiating a measurement spot with a laser further comprises irradiating with a high power level of laser radiation some depth into the formation.

5. The method of claim 1, wherein the generated volatile hydrocarbons and/or pyrolytic hydrocarbons are directed into a measurement device.

6. The method of claim 1, further comprising filtering solid particles from the generated volatile hydrocarbons and pyrolytic hydrocarbons.

7. The method of claim 6, wherein the filtering uses a device selected from the group consisting of an electrostatic solid separator, a screen, and tightly packed particles.

8. The method of claim 1, wherein the measurements are made using a device selected from the group consisting of a mass spectrometer, a photoionization detector, and a thermal conductivity detector.

9. The method of claim 1, wherein the one or more formation properties are selected from the group consisting of detailed hydrocarbon content and total organic content.

10. The method of claim 1, wherein bringing the tool head of the downhole tool into sealing engagement with a wall of the wellbore comprises using a biasing device or a telescoping device.

11. The method of claim 1, further comprising focusing the laser radiation onto a smaller area using a lens.

12. The method of claim 1, wherein the irradiating further comprises using one or more optical fibers to deliver the laser radiation to the measurement spot.

13. A non-transitory, computer-readable storage medium, which has stored therein one or more programs, the one or more programs comprising instructions, which when executed by a processor, cause the processor to perform a method comprising:
   bringing a tool head of the downhole tool into sealing engagement with a wall of the wellbore;
   evacuating fluid within an interior region enclosed by the tool head and the wellbore wall;
   irradiating a measurement spot with a laser to generate volatile hydrocarbons and/or pyrolytic hydrocarbons;
   making measurements on the volatile hydrocarbons and/or pyrolytic hydrocarbons; and
inferring one or more formation properties based on the measurements.

14. The storage medium of claim 13, further comprising irradiating with a low level of laser radiation some or all of the wellbore wall enclosing the interior region, and wherein the irradiating a measurement spot with a laser comprises irradiating first with a medium power level of laser radiation and then with a high power level of laser radiation.

* * * * *